United States Patent [19]

Tanaka et al.

[11] Patent Number: 4,647,408
[45] Date of Patent: Mar. 3, 1987

[54] CARBAPENEM-TYPE ANTIBIOTICS

[75] Inventors: Kentaro Tanaka; Eiji Kondo; Kouichi Matsumoto, all of Osaka; Naoki Tsuji, Hyogo, all of Japan

[73] Assignee: Shionogi & Co., Ltd., Osaka, Japan

[21] Appl. No.: 574,362

[22] Filed: Jan. 27, 1984

[30] Foreign Application Priority Data

Feb. 1, 1983 [JP] Japan ................................. 58-15997
May 9, 1983 [JP] Japan ................................. 58-81325

[51] Int. Cl.$^4$ ..................... C07D 487/04; A61K 31/40
[52] U.S. Cl. ..................................... 540/350; 514/210; 435/119
[58] Field of Search ................ 260/245.2 T, 245.2 R; 424/274, 270; 514/210

[56] References Cited

U.S. PATENT DOCUMENTS 4,210,662  7/1980  Eglington et al. ................... 424/274
4,404,218  9/1983  Ito et al. ......................... 260/245.2 T
4,448,723  5/1984  Tanaka et al. .................... 260/245.2 T

FOREIGN PATENT DOCUMENTS 53-5195    1/1978  Japan .
58-0891    1/1983  Japan .
58-124785  7/1983  Japan .

OTHER PUBLICATIONS

Hood et al., *The Journal of Antibiotics*, vol. 32, No. 4, pp. 295–304 (1979).
Tsuji et al., *The Journal of Antibiotics*, vol. 35, No. 4, pp. 536–540 (1982).
Nakayama et al., *The Journal of Antibiotics*, vol. 34, No. 7, pp. 818–823 (1981).

*Primary Examiner*—Nicholas S. Rizzo
*Attorney, Agent, or Firm*—Wenderoth, Lind & Ponack

[57] ABSTRACT

Antibiotics PA-41746-A$_2$, PA-41746-E and PA-41746-F produced by fermentation of *Streptomyces pluracidomyceticus* on a conventional culture medium, having $\beta$-lactamase inhibitory activities and excellent antimicrobial activities, and useful as drugs for treatment of infections in humans or animals, or as disinfectants.

2 Claims, 4 Drawing Figures

CARBAPENEM-TYPE ANTIBIOTICS

BACKGROUND OF THE INVENTION

1. Field of the Invention

This invention relates to carbapenem compounds. In particular it relates to antibiotics PA-41746-A$_2$, PA-41746-E and the salts thereof having $\beta$-lactamase inhibitory activity, and a process for producing PA-41746-A$_2$, PA-41746-E and/or PA-41746-F by fermentation of *Streptomyces pluracidomyceticus*.

2. Description of the Prior Art

Several carbapenem-type antibiotics produced by Streptomyces and their derivatives have been disclosed. The closely related compounds, each of which has a distinct substituent at the 3-position in the formula (I):

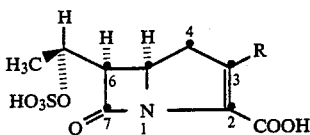

are exemplified below:
MM4550

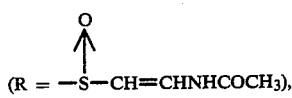
(R = —S—CH=CHNHCOCH$_3$),

MM13902 (R=—SCH=CHNHCOCH$_3$) and MM17880 (R=—S—CH$_2$CH$_2$NHCOCH$_3$) [J. D. Hood et al., The Journal of Antibiotics 32, 295 (1979)], and the oxidized MM17880

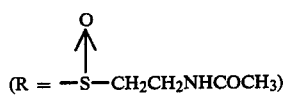
(R = —S—CH$_2$CH$_2$NHCOCH$_3$)

(Jap. Unexam. Pat. Pub. No. 53-5195);
pluracidomycin A (R=—SO$_3$H), pluracidomycin B

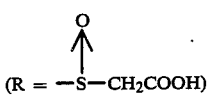
(R = —S—CH$_2$COOH)

and pluracidomycin C

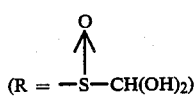
(R = —S—CH(OH)$_2$)

[Naoki Tsuji: The Journal of Antibiotics 35, 536 (1982)], etc.

PA-41746-F in this invention was confirmed to have the same planar structure as the oxidized MM17880 mentioned above has.

SUMMARY OF THE INVENTION

The present invention provides novel compounds of the formula:

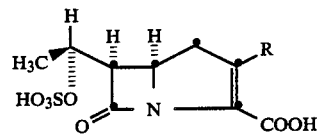

wherein R is —SO$_2$H (PA-41746-A$_2$),

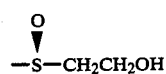

(PA-41746-E) or

(isomer of PA-41746-E); or pharmaceutically acceptable salts thereof, and processes for producing antibiotic PA-41746-A$_2$, PA-41746-E and/or PA-41746-F which comprise culturing a PA-41746-A$_2$-, PA-41746-E- and/or PA-41746-F-producing strain of Streptomyces in a culture medium and recovering at least one of PA-41746-A$_2$, PA-41746-E and PA-41746-F from the culture broth.

DESCRIPTION OF THE PREFERRED EMBODIMENTS

The present invention relates to novel antibiotics PA-41746-A$_2$, PA-41746-E and the isomer of PA-41746-E and a process for producing them. In this invention, the known antibiotic PA-41746-F is also produced together with the above new antibiotics. The present inventors have found that some organisms belonging to *Streptomyces pluracidomyceticus* which produce pluracidomycins as mentioned above, also produce carbapenem-type antibiotics PA-41746-A$_2$, PA-41746-E and PA-41746-F; the present invention is based on this finding.

Sodium salts of PA-41746-A$_2$, E and F of this invention have the following physical properties, from which the structural formula of them were identified.

(a)

Ultraviolet Absorption Spectrum:

|  | PA-41746-A$_2$ | PA-41746-E | PA-41746-F |
|---|---|---|---|
| $\gamma_{max}^{H_2O}$:nm | 273 | 287 | 280 |

(b)

Infrared Absorption Spectrum:

| | $U_{max}^{KBr}$cm$^{-1}$ | | | | |
|---|---|---|---|---|---|
| PA-41746-A$_2$ | 3440, | 1760, | 1610, | 1395, | 1250, |

-continued

Figure 1:
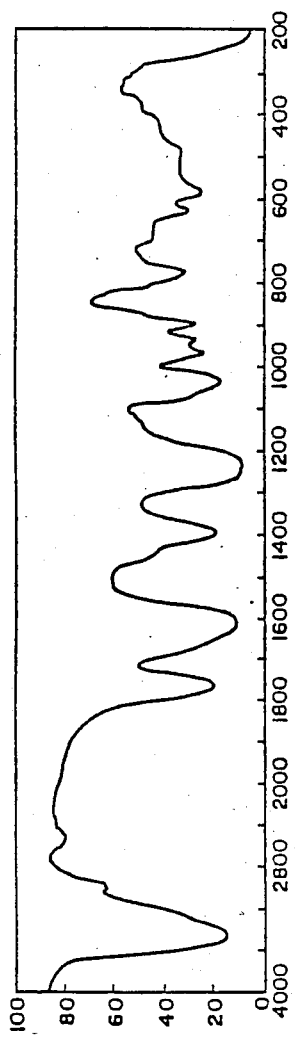
FIG. 1 shows an infrared absorption spectrum of PA-41746-A$_2$ in a KBr disc.

| $U_{max}^{KBr}$cm$^{-1}$ |
| --- |
| 1220, 1030, 965, 935, 896. (FIG. 1) |

(c)

$^1$H-nuclear Magnetic Resonance Spectrum: (In heavy water, external standard TMS, 200 MHz)

Figure 2:
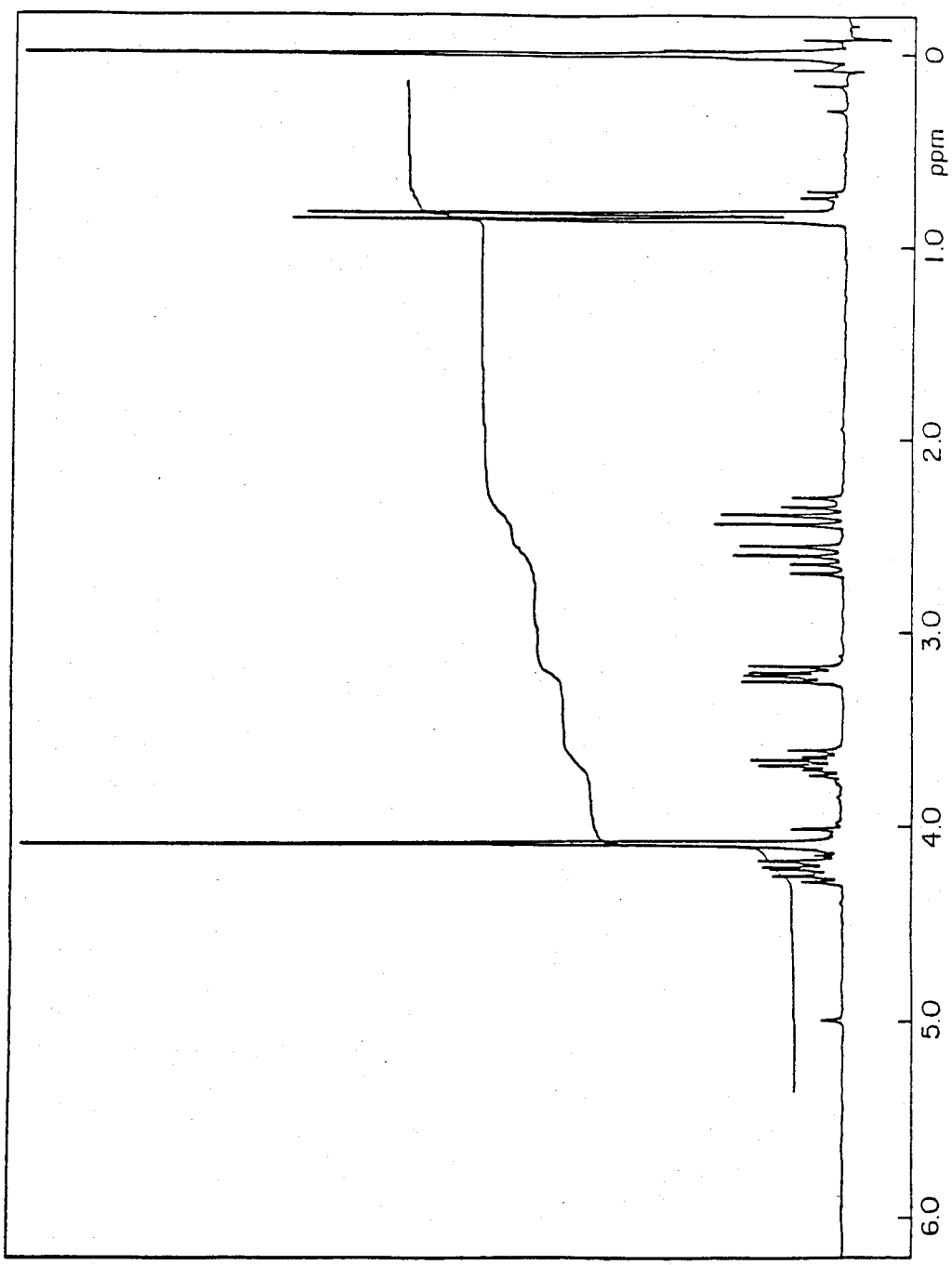
FIG. 2, FIG. 3 and FIG. 4 show $^1$H-nuclear magnetic resonance spectra of PA-41746-A$_2$, PA-41746-E and PA-41746-F, respectively, in heavy water.
Figure 3:
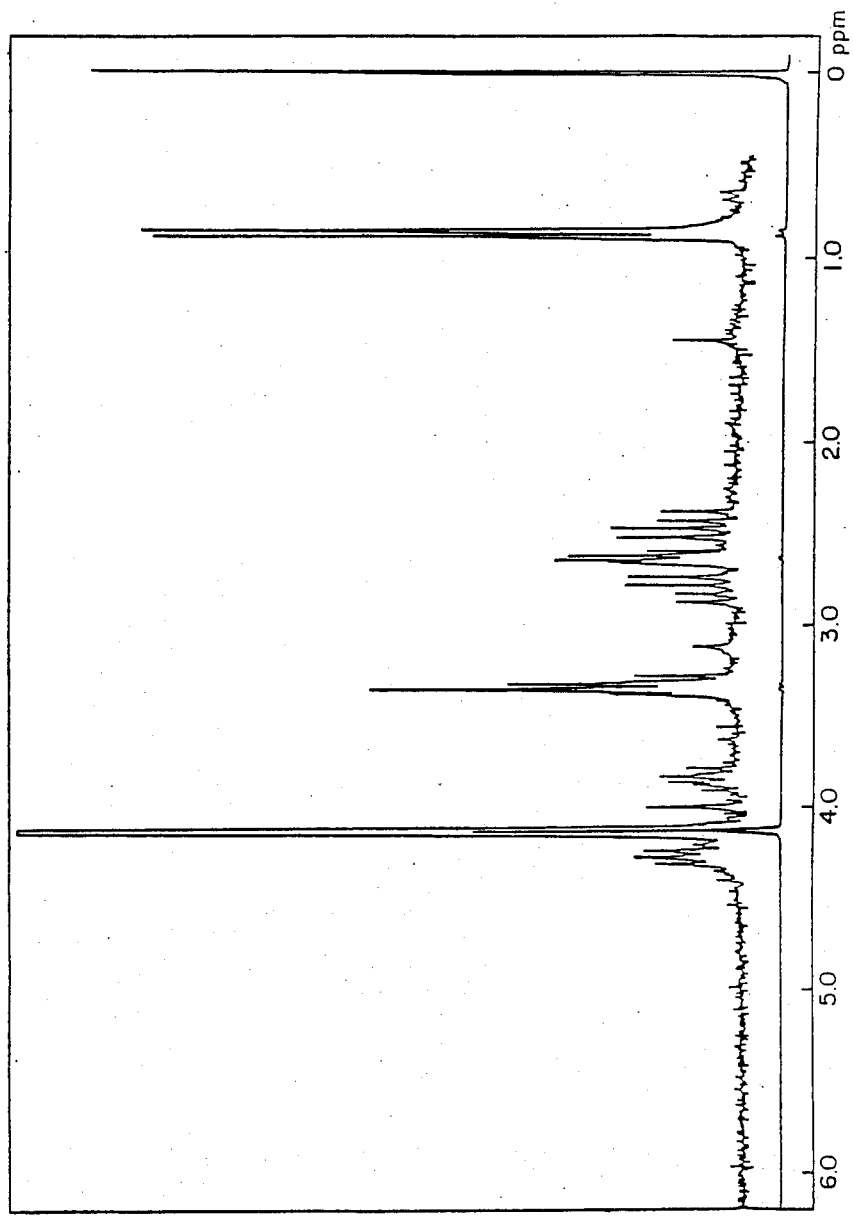
Figure 4:
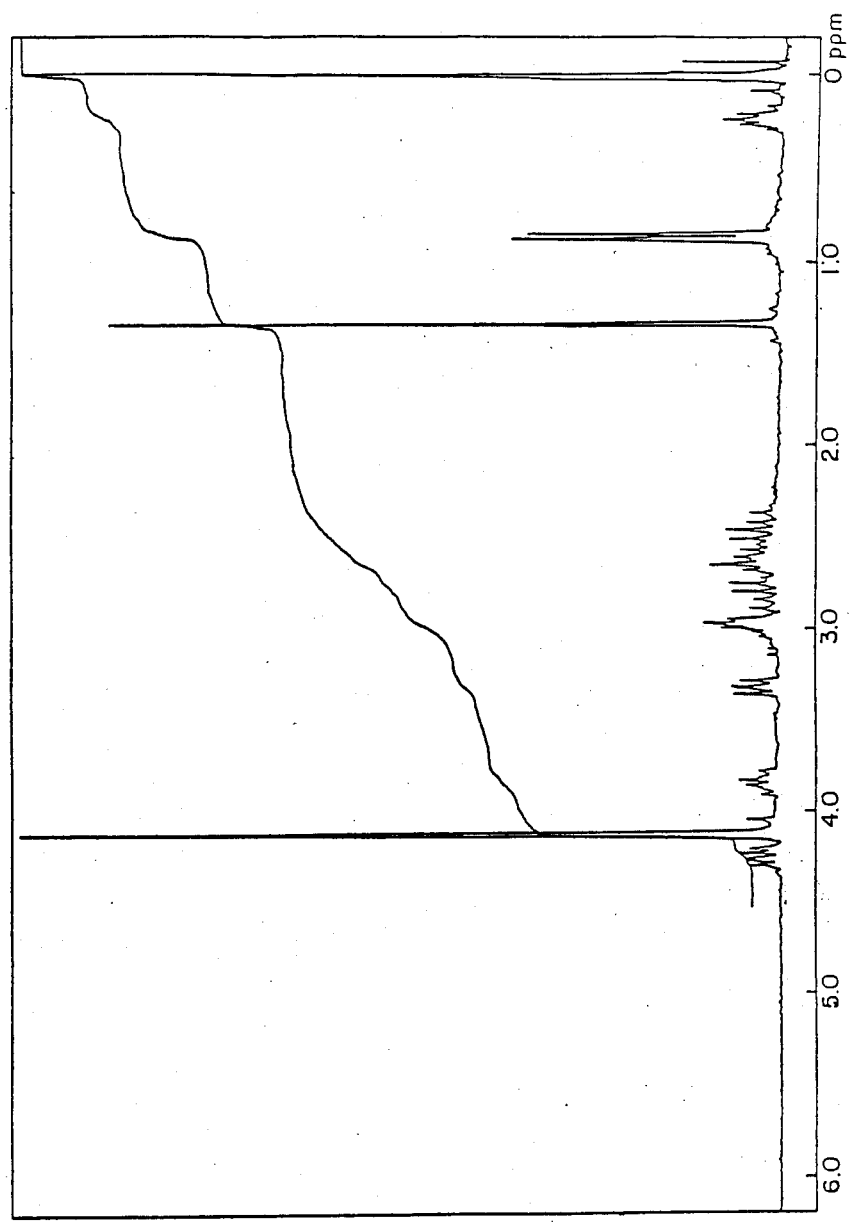

| | $\delta_{ppm}$ (J=Hz) |
| --- | --- |
| PA-41746-A$_2$ | 0.84 (3H, d, J=6.1), −2.37 (1H, d–d, J=10.2 18.0), −26.3 (1H, d–d, J=9.4, 18.0), 3.21 (1H,d–d, J=5.8, 9.0), 3.67 (1H, m), 4.21 (1H,m). (FIG. 2) |
| PA-41746-E | 0.88 (3H, d, J=6), 2.48 (1H, d–d, J=10.5, 18), 2.66 (2H, m), 2.82 (1H, d–d, J=9, 18), 3.32 (1H, d–d, J=6, 9), 3.36 (2H, m), 3.84 (1H, m), 4.28 (1H, m). (FIG. 3) |
| PA-41746-F | 0.86 (3H, d, J=6), 1.34 (3H, s), 2.43 (1H, d–d, J=10.5, 18), 2.62 (2H,m), 2.81 (1H, d–d, J=9, 18), 2.96 (2H, m), 3.31 (1H, d–d, J=5.5, 9), 3.83 (1H, m), 4.26 (1H, m). (FIG. 4) |

(d)

High Performance Liquid Chromatography:

(1) PA-41746-A$_2$

Column: Nucleosil $_7$C$_{18}$ (made by M. Nagel) $\phi$4.6 mm×150 mm

Mobile phase: A mixture (1000 ml) of 10% aqueous tetraethylammonium hydroxide (7.12 g), 10% aqueous tetrapropylammonium hydroxide (0.34 g), disodium hydrogenphosphate dodecahydrate (0.5 g) and a proper quantity of water is adjusted at pH 7.0 by addition of aqueous sodium dihydrogenphosphate.

Flow rate: 1.5 ml/min.

| | Retention Time (min.) |
| --- | --- |
| PA-41746-A$_2$ | 5.2 |
| pluracidomycin-A | 7.5 |
| pluracidomycin-C | 6.5 |

(2) PA-41746-E, PA-41746-F

Column: Nucleosil $_7$C$_{18}$, $\phi$4 mm×200 mm

Mobile phase: 0.05M phosphate buffer (pH 7.0)

Flow rate: 1 ml/min.

| | Retention Time (min.) |
| --- | --- |
| PA-41746-E | 3.5 |
| PA-41746-F | 5.8 |

(e) Electrophoresis [Toyo filter paper No. 131, 1/30M phosphate buffer (pH 7.0), 12 v/cm, for 1.5 hours]:

| | Relative Mobility |
| --- | --- |
| PA-41746-A$_2$ | 3.0 |
| pluracidomycin A | 3.0 |
| pluracidomycin B | 2.7 |
| pluracidomycin C | 1.9 |
| epithienamycin A | 1.0 |

On the basis of the above properties, PA-41746-A$_2$, PA-41746-E and PA-41746-F were elucidated to respectively have —SO$_2$H,

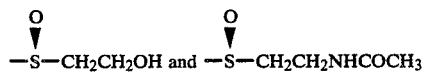

at the 3-position of the aforementioned formula (I), whereby PA-41746-A$_2$ and PA-41746-E were confirmed to be novel antibiotics distinct from the already-known carbapenem-type ones. On the other hand, PA-41746-F has the same planar structural formula as the already-known compound which is prepared from the aforementioned MM17880 by oxidation [disclosed in Jap. Unexam. Pat. Pub. No. 53-5195; Eglington et al. (Beecham Group Ltd.)]; the oxidation of MM17880, however, gave a 1 to 1 mixture of the steric isomers at the S-oxide portion. The fermentation process of the present invention gives only the (R)-S-oxide isomer, i.e. PA-41746-F.

The present invention includes PA-41746-A$_2$ and E and pharmaceutically acceptable salts thereof (e.g., sodium salt, potassium salt, calcium salt, etc.).

PA-41746-A$_2$, E and F, as mentioned above, are produced by Streptomyces pluracidomyceticus PA-41746 which also produces pluracidomycin A, B and C. The bacteriological characteristics of the organism are disclosed in the Jap. Unexam. Pat. Pub. No. 58-891, in which pluracidomycin A is called PA-41746-A.

The type culture of the strain has been deposited by the name of Streptomyces sp. PA-41746 as FERM BP-174 with Fermentation Research Institute Agency of Industrial Science & Technology at 1-3, Higashi 1 chrom Yatabe-machi, Tsukuba-gun, Ibaraki-ken 305, Japan since May 1, 1981.

The present invention includes all the processes for producing PA-41746-A$_2$, E and/or F not only by the aforementioned Streptomyces pluracidomyceticus PA-41746 but also by other PA-41746-A$_2$, E and/or F producing strains of Streptomyces.

The fermentation process for producing PA-41746-A$_2$, E and/or F is shown as follows.

They may be obtained by incubating PA-41746-A$_2$, E and/or F producing microorganisms in a nutrient medium under an aerobic condition and recovering the accumulated PA-41746-A$_2$, E and/or F from the culture broth.

The culture medium and culture conditions may be fixed according to a usual way generally employed in the production of antibiotics. The medium generally contains carbon sources, nitrogen sources, minerals and the like. If necessary, vitamins, precursors and other additives may be added to the medium in order to increase the yield of PA-41746-A$_2$, E and/or F. As a carbon source, glucose, starch, dextrin, glycerol, molasses, organic acid and the like may be employed singly or as a mixture of them. As a nitrogen source, soybean meal, corn steep liquor, meat extract, yeast extract, cotton seed meal, peptone, wheat germ, ammonium sulfate, ammonium nitrate and the like may be employed singly or as a mixture of them. Mineral sources such as calcium carbonate, sodium chloride, potassium chloride, magnesium sulfate, cobalt chloride and various kinds of phosphates may be added to the nutrient medium according to the necessities.

The cultivation may be carried out according to a conventional manner generally used in the production of antibiotics, preferably in the condition of liquid cultivation, particularly submerged culture condition under aeration on a large scale production. The pH in the medium is preferably maintained in a range of about 5.5–about 8.5, the temperature for the incubation at about 20°–about 40° C., particularly at 25°–32° C. The incubation period is greatly influenced by the scale of fermentation, and in case of a large scale production, the incubation may be effected for a period of about 20–about 80 hours.

After the termination of the cultivation, PA-41746-$A_2$, E and/or F can be recovered from the culture medium in a conventional manner for recovering usual fermentation products. For example, it is preferably accomplished in combination with such techniques or methods as filtration, centrifugal separation, adsorption or desorption with various kinds of ion-exchange resin or other active adsorbents, chromatography, extraction with various kinds of organic solvents and the like. Additionally, it may be taken into account to employ, if required, a suitable stabilizer in the separation step in order to prevent PA-41746-$A_2$, E and/or F from decomposition. Formation of salt of them may be considered for convenience in the separation and purification. PA-41746-$A_2$, E and/or F are expected to be accompanied by pluracidomycin A, B, C or D as by-product, which can readily be removed in a conventional technique such as chromatography, extraction, etc. PA-41746-$A_2$, E and/or F obtained as free acids, if required, may be formed into the salts in a conventional manner.

As mentioned above, Eglington et al. have disclosed that the oxidized MM17880 (corresponding to our PA-41746-F) is obtained as a 1 to 1 mixture of its steric isomers at the S-oxide portion (Jap. Unexam. Pat. Pub. No. 53-5195). It is well known in the field of organic chemistry that in chemical synthesis, such a compound is given as a mixture of the steric isomers of R- and S-configurations at the S-oxide portion, but on the contrary the fermentation process gives the R-configuration (The Journal of Antibiotics 34, 818(1981)). PA-41746-E and F each is obtained as the (R)-S-oxide in the present invention and each of them can be epimerized into the (R)- and (S)-S-oxide mixture as exemplified below: PA-41746-E and F are deoxidized according to the same manner as disclosed in Jap. Unexam. Pat. Pub. No. 58-124785 in which the pluracidomycin B or C is deoxidized, and then oxidized according to the Eglington et al. manner of oxidation with an organic peracid (Jap. Unexam. Pat.Pub. No.53-5195), whereby PA-41746-E and F can be obtained as the (R)- and (S)-oxide mixture, which may be separated into the (R)- and (S)-isomers in a conventional manner.

PA-41746-$A_2$, E and F have not only antimicrobial activities against Gram-positive and Gram-negative microorganisms, but also excellent β-lactamase inhibitory activities. Results of the tests on the antimicrobial activities and β-lactamase inhibitory activities are summarized as follows.

(1) Antimicrobial Activity:

| Test microorganism | PA-41746-$A_2$ Minimum Inhibitory Concentration (μg/ml) |
|---|---|
| Staphylococcus aureus 209P JC-1 | 12.5 |
| Streptococcus pneumoniae I | 1.56 |
| Escherichia coli NIHJ JC-2 | 1.56 |
| Klebsiella pneumoniae SRL-1 | 1.56 |
| Klebsiella sp. 363(R) | 1.56 |
| Proteus mirabilis PR-4 | 3.13 |
| Enterobacter cloacae 233 | 6.25 |
| Pseudomonas aeruginosa ATCC 25619 | >100 |

Note:
Determined by agar dilution method: Inoculum size $10^6$ cells/ml, Cultivation on a sensitivity-disc agar medium at 37° C. overnight.

(2) Test on the β-lactamase inhibitory activity:

The β-lactamase inhibitory activity is expressed as a minimum concentration (μg/ml) of the test compound which is required to inhibit the hydrolysis of the substrate by β-lactamase. The supernatant, which has been obtained by means of breaking the washed cells of the β-lactamase-producing microorganisms in a buffer with ultrasonic waves and then centrifuging the consequent cell-free extract, is employed as a standard β-lactamase.

Test Method:

A test compound is successively diluted with a buffer (pH 7.0) by a two-fold dilution method, the standard β-lactamase in added to each of the diluted solutions, then the mixture is allowed to stand for 10 minutes, and an indicator is added therein. The minimum inhibitory concentration at which no color is developed after observation for 20 minutes, is determined.

| Source of β-lactamase | Minimum Inhibitory Concentration (μg/ml) | | |
|---|---|---|---|
| | PA-41746-$A_2$ | PA-41746-E | PA-41746-F |
| Enterobacter cloacae 92[*1] | 0.008 | 0.016 | 0.002 |
| Klebsiella sp. 363[*2] | 1.0 | 0.008 | 0.002 |
| | 1.0 | 0.008 | 0.002 |

[*1]Producing cephalosporinase-type β-lactamase
[*2]Producing penicillinase-type β-lactamse As mentioned above, each of PA-41746-$A_2$, E and F is a useful compound as a drug for human or veterinary use, or a disinfectant, because of having a β-lactamase inhibitory activity as well as an antimicrobial activity against both Gram-positive and Gram-negative microorganisms.

Therefore, PA-41746-$A_2$, E or F can be administered orally or parenterally to humans or animals. They may be administered in oral preparations such as tablets, capsules and powders which are formulated with conventional excipients, stabilizers, preservatives, wetting agents, surfactants and the like; or in paranteral preparations such as injections, liniments and suppositories. The dose of PA-41746-$A_2$, E or F which varies according to the aim or the object to be treated, is generally about 1/10–several times of that of cefalotin; for example, it may be subcutaneously administered at about 0.1–30 g per day for an adult.

Furthermore, PA-41746-$A_2$, E and/or F can also be used in synergistically increasing the antimicrobial activities of β-lactam antibiotics against β-lactamase producing microorganisms since they have β-lactamase inhibitory activities. Therefore they may be administered together with known β-lactam antibiotics, for example, penicillin-type ones such as benzylpenicillin, phenoxymethylpenicillin, carbenicillin, ampicillin, amoxicillin; or cephalosporin-type ones such as cefaloridine, cefalotin, cefazolin, cefalexin, cefoxitin, cephacetril, cefamandole, cephapirin, cephradin, cefaloglycin, ceftezole, cefatrizine and the like.

PA-41746-$A_2$ may also be employed as an intermediate for pluracidomycin A. As mentioned above, PA-41746-$A_2$ has a sulfino group at the 3-position, which corresponds to the 3-sulfo group in pluracidomycin A. Accordingly, it can readily be converted into pluracidomycin A by means of oxidation with potassium permanganate, sodium permanganate, hydrogen peroxide, organic peracids and the like in a suitable solvent such as acetic acid, acetone, water and the like.

The following examples serve to illustrate the practical production and formulation of the objective compound PA-41746-$A_2$, E and/or F in this invention, but those are not intended to limit the scope of this invention.

EXAMPLE 1

(a)

Fermentation Step

A seed slant culture of *Streptomyces pluracidomyceticus* PA-41746(FERM BP-174) was inoculated in a culture medium (800 ml) consisting of soluble starch (0.5%), glucose (0.5%), polypeptone (0.5%), meat extract (0.5%), yeast extract (0.25%), sodium chloride (0.25%) and deionized water (pH 7.0, before pasteurization) placed in a 2 L Erlenmeyer flask and cultured with shaking (at 180 r.p.m.) at 28° C. for 48 hours. The culture broth (800 ml) was inoculated in a culture medium (20 L) placed in a 30 L jar fermenter, consisting of tomato paste (2.4%), dextrin (2.4%), dry yeast (1.2%), cobalt chloride hexahydrate (0.0006%) and water (pH 7.0, before pasteurization) and then cultured under aeration of 20 L/min. and internal pressure of 0.2 kg/cm$^2$, with shaking of 150–350 r.p.m. at 28° C. for 65 hours.

(b)

Separation Step (1) PA-41746-$A_2$

Disodium ethylenediaminetetraacetate (hereinafter referred to as EDTA) was added into the culture broth obtained above so as to be 50 Ξ/ml content, from which 160 L of the supernatant was obtained by centrifugation with a Scharples-type centrifuge. The supernatant was cooled to 10° C., to which 40 L of methylene chloride containing 1.2% benzylcetyldimethylammonium chloride was added. The active portion was moved into methylene chloride layer, which was then extracted with 3% aqueous solution (3 L) of sodium iodide and lyophilized to give an active material (187 g) as crude powder.

The crude product (20 g) was dissolved in 100 ml of water and desalted by treatment with 600 ml of Biogel P-2 (made by Bio-Rad Lab.). The active fraction was lyophilized to give a lyophilizate (16.1 g). This (8 g) was dissolved in 600 ml of water and passed by a gradient method through 130 ml of QAE-Sephadex A-25(Cl$^-$ type; Pharmacia AB.) with 0–3% sodium chloride solution (0.005M; added ammonium chloride) as an eluent. The fraction containing PA-41746-$A_2$ was eluted between pluracidomycin A and pluracidomycin B fractions. The fraction of PA-41746-$A_2$ was concentrated while being kept at pH 6.8, desalted through a column of 250 ml of Biogel P-2 and then lyophilized to give 300 mg of PA-41746-$A_2$ as a crude product. The product (600 mg) was passed through a column of HP-20AG (made by Mitsubishi Chem. Ind.) with 15% sodium chloride solution as an eluent. The active fractions showing a single peak on High Performance Liquid Chromatography (HPLC) were collected, adjusted to pH 6.8, condensed in vacuo, then desalted with Biogel P-2 and lyophilized to give a pure product (22 mg).

(2) PA-41746-E and PA-41746-F

To the culture broth (240 L) obtained in the above step (a) was added methylene chloride (60 L) containing 1.2% benzylcetyldimethylammonium chloride. The active portion was moved into methylene chloride layer, which was then extracted with 3% aqueous solution (5 L) of sodium iodide and lyophilized to give an active material (138 g).

The crude powdery product (20 g) was dissolved in water and gel-filtrated with 600 ml of Biogel P-2 (made by Bio-Rad Lab.). The active fractions which show the activity against *Escherichia coli* were collected and then lyophilized to give lyophilizate (0.5 g). This (3.5 g) was passed by a gradient method through QAE-Sephadex A-25(Cl$^-$ type, made by Pharmacia AB.) with 0.3–3.0% sodium chloride solution (0.05M, added ammonium chloride) as an eluent to give the C-fraction (290 ml), B-fraction (130 ml) and A-fraction (330 ml) in order.

The C-fraction containing pluracidomycin C was desalted through a column of Biogel P-2, adjusted at pH 6.4, concentrated in vacuo, and then lyophilized to give an active material (253 mg). This was passed through a column of HP-20AG (made by Mitsubishi Chem. Ind.) with 10% aqueous sodium chloride as an eluent. After eluation of the fraction (about 30 ml) containing pluracidomycin C, the fractions containing PA-41746-E and F can be obtained with an additional amount of 2% aqueous sodium chloride. Each fraction was desalted through a column of Biogel P-2. The fractions containing active material were collected, then adjusted at pH 6.4, concentrated in vacuo and lyophilized to give the sodium salt (13 mg) of PA-41746-E and the sodium salt (9 mg) of PA-41746-F as crude powders.

The crude powder obtained from the C-fraction was chromatographed on HPLC through a column of Nucleosil-$7C_{18}$ (made by M. NAGEL, $\phi$10 mm×300 mm) with 0.05M phosphate buffer (pH 6.5) as a mobile phase to give active fractions, which were collected and adsorbed on a column of HP-20AG previously treated with 15% aqueous sodium chloride. Then the column was eluted with water, and the eluate was desalted with Biogel P-2, concentrated in vacuo and then lyophilized to give the sodium salt (1 mg) of PA-41746-E as powder.

The crude powder of F-fraction was charged on a column of HP-20AG previously treated with 3% aqueous sodium chloride, and eluted with the same solution. The active fractions were collected, desalted with Biogel P-2, concentrated in vacuo and then lyophilized to give the sodium salt (3 mg) of PA-41746-F as powder.

EXAMPLE 2

Disodium salt (100 mg) of PA-41746-$A_2$, sodium monohydrogenphosphate and sodium dihydrogenphosphate (necessary amount) are dissolved in 4 ml of pasteurized water to give a preparation for injection.

EXAMPLE 3

PA-41746-A$_2$ (100 mg), corn starch (150 mg), magnesium stearate (10 mg) and talc (10 mg) are admixed to give a powder preparation.

EXAMPLE 4

In the same manner as in Example 2, disodium salt (100 mg) of PA-41746-E is formulated into a preparation for injection.

EXAMPLE 5

In the same manner as in Example 3, PA-41746-E (100 mg) is formulated into a powder preparation.

What is claimed is:

1. A compound of the formula:

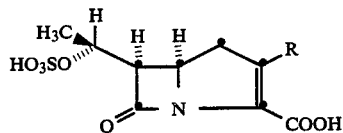

wherein R is —SO$_2$H, or a pharmaceutically acceptable salt thereof.

2. An antimicrobial composition which comprises an anti-microbially effective amount of a compound or a pharmaceutically acceptable salt thereof according to claim 1 and a pharmaceutically acceptable carrier therefor.

* * * * *